United States Patent
Trau (10) Patent No.: US 10,082,884 B2
(45) Date of Patent: Sep. 25, 2018

(54) METHOD AND HAND HELD LABORATORY DEVICE TO CONTROL SCREEN NAVIGATION

(71) Applicant: National University of Singapore, Singapore (SG)

(72) Inventor: Dieter Wilhelm Trau, Singapore (SG)

(73) Assignee: National University of Singapore, Singapore (SG)

( * ) Notice: Subject to any disclaimer, the term of this patent is extended or adjusted under 35 U.S.C. 154(b) by 22 days.

(21) Appl. No.: 15/035,628

(22) PCT Filed: Nov. 13, 2014

(86) PCT No.: PCT/SG2014/000533
§ 371 (c)(1),
(2) Date: May 10, 2016

(87) PCT Pub. No.: WO2015/072924
PCT Pub. Date: May 21, 2015

(65) Prior Publication Data
US 2016/0299577 A1    Oct. 13, 2016

(30) Foreign Application Priority Data
Nov. 13, 2013 (GB) .................................. 1320019.1

(51) Int. Cl.
| | |
|---|---|
| *G09G 5/00* | (2006.01) |
| *G06F 3/0346* | (2013.01) |
| *G06F 1/16* | (2006.01) |
| *G06F 3/01* | (2006.01) |
| *G06F 19/00* | (2018.01) |

(52) U.S. Cl.
CPC .......... *G06F 3/0346* (2013.01); *G06F 1/1694* (2013.01); *G06F 3/017* (2013.01); *G06F 19/00* (2013.01); *G06F 19/30* (2013.01)

(58) Field of Classification Search
CPC ...... G06F 3/017; G06F 3/0346; G06F 3/0487; G06F 3/0488; G06F 3/04883
See application file for complete search history.

(56) References Cited

U.S. PATENT DOCUMENTS

| | | | |
|---|---|---|---|
| 6,573,883 B1 | 6/2003 | Bartlett | |
| 8,159,457 B2* | 4/2012 | Coe | G06F 3/017 345/157 |
| 8,482,678 B2* | 7/2013 | Sun | G06F 3/017 348/552 |
| 9,076,322 B2* | 7/2015 | Patel | G08C 17/00 |
| 9,424,738 B2* | 8/2016 | Patel | G08C 17/00 |
| 9,685,072 B2* | 6/2017 | Patel | G08C 17/00 |
| 2008/0074391 A1 | 3/2008 | Coe | |
| 2011/0058107 A1 | 3/2011 | Sun et al. | |
| 2012/0174164 A1 | 7/2012 | Patel et al. | |

FOREIGN PATENT DOCUMENTS

DE          10149879       12/2004

* cited by examiner

*Primary Examiner* — Vijay Shankar
(74) *Attorney, Agent, or Firm* — Cesari and McKenna, LLP (57) ABSTRACT

A method and a hand held laboratory device to control screen navigation on a display instrument such as a smart phone or tablet computer by using predetermined movements of the hand held device caused by the user. The display instrument controls the hand held laboratory device, which allows the user of a hand held device to operate the device without the need of touching the display instrument.

15 Claims, 3 Drawing Sheets

METHOD AND HAND HELD LABORATORY DEVICE TO CONTROL SCREEN NAVIGATION

CROSS REFERENCE TO RELATED APPLICATIONS

This application is the National Stage of International Application No. PCT/SG2014/000533, filed on Nov. 13, 2014, which claims the benefit of Great Britain Application No. 1320019.1, filed on Nov. 13, 2013. The contents of both applications are hereby incorporated by reference in their entirety.

FIELD OF INVENTION

The current invention relates to a method and a hand held laboratory device to control screen navigation on a display instrument such as a smart phone or tablet computer by using predetermined movements of the hand held device caused by the user. The display instrument then controls the hand held laboratory device. This allows the user of a hand held device to operate the device without the need of touching the display instrument. This is of uttermost importance if the user use gloves contaminated with a toxin or microbes or if the hand held device is operated under a fume hood or laminar flow bench.

BACKGROUND OF THE INVENTION

Most laboratory instruments are of the bench top type. In recent years also some hand held devices were introduced into laboratories. For example a hand held device to count cells. Trau et all proposed a hand help photometer device. The background of the current invention will be further illustrated on the example of a hand help photometer. It is noted here that this should not be interpreted as a limitation of the current invention. In general, the invention can be applied to all types of hand help laboratory devices such as photometers, pH meters; volt, conductivity and ampere meters; gas sensors, glucose meters, biosensors, luminometers, blood pressure meters, radiometers, temperature and pressure meters and more.

Photometry is an important analytical method with various applications. The current state of the art photometric apparatus is usually a bench top instrument. Photometers can be divided into two groups, instruments using cuvettes and instruments using an immersible sensor. Cuvette based instruments are usually heavy desktop instruments or smaller portable instruments with reduced functions. Most instruments using immersible sensors are comprised of a desktop unit connected to the immersible sensor via a light guiding glass fiber. Trau and Orban (DE 10149879) describe a handheld photometer using a disposable and immersible sensor tip with a cuvette recess function. The photometer of the teachings of Trau also contains electronic to analyse and process the measurement results and a display to display the results on the device. The device is controlled by using at least one conventional push button for pressing. All existing laboratory hand held devices are working in the same way using conventional means of user input and control such as push buttons and a display to display results and operation modes or error messages. This conventional way of operation has several disadvantages. For example the user may needs his other hand to push a button on the device he is holding. The control is also minimal with only a small number of buttons on the device. In the current invention we overcome those limitations by introducing a method to control screen navigation on another display device by predetermined movements of the hand held device.

SUMMARY OF THE INVENTION

According to a first aspect of the invention there is provided a method of operating a display device for a hand held laboratory device, the display device comprising a screen, the method comprising the steps of receiving acceleration data from an accelerometer of the hand held laboratory device, computing a movement of the hand held laboratory device from the acceleration data, comparing the computed movement with a predetermined set of movements and where the computed movement matches or is similar to one of the predetermined set of movements, initiating a screen navigation function on the screen corresponding to the matched predetermined movement and/or initiating a control function in the hand held laboratory device corresponding to the matched predetermined movement; for example to operate the measurement means such as light sources or sensors.

The method may comprise receiving acceleration data from at least one accelerometer in the hand held laboratory device and computing a movement of the hand held laboratory device by computing a trajectory of the movement of the hand held laboratory device.

The method may comprise comparing the computed trajectory with predetermined movements or trajectories to match the computed trajectory with one predetermined movement.

The method may comprise receiving acceleration or movement data from at least one of a position sensor and an accelerator of the display device, and using the movement or acceleration of the display device in computing the movement of the handheld laboratory device.

The steps of receiving acceleration data from an accelerometer of the hand held laboratory device and computing a movement of the hand held laboratory device from the acceleration data may be performed at the hand held laboratory device.

The step of comparing the computed movement with a predetermined set of movements may be performed at the hand held medical device.

The steps of receiving acceleration data from an accelerometer of the hand held laboratory device and computing a movement of the hand held laboratory device from the acceleration data may be performed at the display device.

The step of comparing the computed movement with a predetermined set of movements may be performed at the display device.

The predetermined movement may be one or more of a tilting movement, movements away or towards the user, movements to the right or left of the user, movements up and down, circular movements clockwise or anti clockwise, spinning movements clockwise or anti clockwise, shaking movements, no movement (still stand) or a combination of such movements.

The method may comprise computing the movements of the handheld laboratory device relative to the hand held laboratory device or relative to the user or relative to a fixed coordinate system in space.

The screen navigation function may be one or more of scrolling of a screen, opening a new screen, selecting a function or tap on a screen, taping a tap, browse through a sequence of taps or functions for selection, switch to cursor movement and back, editing a screen, start a program, closing a program.

The method may comprise transmitting data from at least one accelerometer of the handheld laboratory device to a display device.

According to a second aspect of the invention there is provided a program operable when run on the hand held measurement device and/or the display device to perform a method according to the first aspect of the invention.

According to a third aspect of the invention there is provided a handheld laboratory device comprising measurement means and at least one accelerometer, the handheld laboratory device being operable to movement data from the at least one accelerometer to a display device.

The handheld laboratory device may be a wireless handheld laboratory device comprising measurement means and at least one accelerometer and wherein a movement of the handheld laboratory device in a 3 dimensional x,y,z coordinate system is wireless relayed to a display device to compute instructions for the handheld laboratory device to operate the measurement means.

The hand held laboratory device may be operable to receive acceleration data from the accelerometer of the hand held laboratory device and compute a movement of the hand held laboratory device from the acceleration data.

The movement data may comprise the computed movement of the hand held device.

The hand held laboratory device may be operable to compare the computed movement with a predetermined set of movements.

The hand held laboratory device may be operable, where the computed movement matches or is similar to one of the predetermined set of movements, to transmit movement data comprising the one of the predetermined set of movements to the display device.

The measurement means may comprise one of more of a photometer, a spectrometer, a pH meters, a volt, conductivity or ampere meter; a luminometer, a gas detection meter, a pipette, a turbidity meter, a nephleometer, a temperature or pressure meter, a x-ray detection meter, a scanners for drugs or explosives, a glucose meter, a biosensor, a point of care diagnostic device, a blood pressure meter or mixtures thereof.

According to a fourth aspect of the invention there is provided a display device for a hand held laboratory device, the display device containing a screen, the display device being operable to a receive movement data from a hand held movement data from the hand held laboratory device and initiate a screen navigation function on the screen corresponding to the movement data.

Where the movement data comprises acceleration data from the hand held laboratory device, the display device may be operable to compute a movement of the hand held laboratory device from the acceleration data, compare the computed movement with a predetermined set of movements and where the computed movement matches or is similar to one of the predetermined set of movements, initiate the screen navigation function.

The display device may be operable to compute a movement of the hand held laboratory device by computing a trajectory of the movement of the hand held laboratory device.

The movement data may comprise a computed trajectory

The display device may be operable to compare the computed movement with the predetermined set of movements by comparing the computed trajectory with predetermined movements or trajectories to match the computed trajectory with one predetermined movement.

The display device may be a smartphone, a tablet computer or a personal computer or a notebook computer or a dedicated device built to work with the hand held laboratory device.

The display device may comprise at least one of a position sensor and an accelerator, wherein the program is operable to use the movement or acceleration of the display device in computing the movement of the handheld laboratory device.

The predetermined movement may be tilting movements, movements away or towards the user, movements to the right or left of the user, movements up and down, circular movements clockwise or anti clockwise, spinning movements clockwise or anti clockwise, shaking movements, no movement (still stand) or a combination of such movements.

The display device may be operable to compute the movements of the handheld laboratory device relative to the hand held laboratory device or relative to the user or relative to a fixed coordinate system in space.

The screen navigation function may be the scrolling of a screen, opening a new screen, selecting a function or tap on a screen, taping a tap, browse through a sequence of taps or functions for selection, switch to cursor movement and back, editing a screen, start a program, closing a program.

The control function in the hand held laboratory device may be to switch the device on or off, start a measurement, stop a measurement, send data to the display device, switch on or of a light source, switch on or of a sensor, switch on or of an indicator light, determine the status of a button, receive data from the display device, display information on a display in the hand held device, send battery status information, send error messages, and mixtures thereof.

According to a fifth aspect of the invention there is provided a system comprising a hand held laboratory device according to the third aspect of the invention and a display device according to the fourth aspect of the invention.

The current invention teaches a method and a hand held laboratory device to control screen navigation on a display instrument such as a smart phone or tablet computer by using predetermined movements of the hand held device. A predetermined movement of the hand held device by the user following a predetermined trajectory. Several predetermined movements and trajectories can be defined such as tilting movements, movements away or towards the user, movements to the right or left of the user, movements up and down relative to the user, circular movements clockwise or anti clockwise, spinning movements clockwise or anti clockwise, shaking movements or a combination of such movements. The predetermined movement will lead to acceleration of the device, the acceleration can be positive or negative and can be in all directions of a 3-axis x,y,z coordinate system relative to the user or relative to the hand held device. The acceleration is detected by at least one accelerator in the device and wireless transmitted to a display device. Depending of the predetermined movement transmitted to the display device a respective screen navigation operation such as scrolling of a screen or selecting a function on the screen is initiated. The invention overcomes several limitations of current hand held laboratory instruments. Advantageously, the user of the hand help laboratory device can perform screen navigation on a display device without touching the display device. The current invention enables a hand free operation of a display device such as a smart phone. This is in particular important in the laboratory environment at which the user may use gloves contaminated with a toxin or microbes or the user works in a fume hood or the user works under a laminar flow bench in a sterile environment.

DEFINITIONS

The term "hand held device" or "hand held laboratory device" means a mobile device operated by holding it in the hand of the operator or user such as but not limited to photometers, spectrometers, UV or visual or infrared spectrometers, pH meters; volt, conductivity and ampere meters; luminometers, gas detection meters, pipettes, turbidity meter, nephleometer, temperature and pressure meters, x-ray detection meters, scanners for drugs or explosives, spectrometers and more. In general the term applies to all hand held devices used in a laboratory or used for measurements outside of a laboratory such as environmental measurements. In the context of the current invention the term also includes point-of-care devices for diagnostic and medical applications used by medical personal or a patient such as but not limited to glucose meters, biosensors, blood pressure meters, thermometers, and photometers. The hand held device of the current invention contains at least one accelerometer to detect movements of the device. The hand held device of the current invention may be wireless and transmit data remotely.

The term "predetermined movement" means a movement of the hand held device by the user or operator following a predetermined trajectory. Several predetermined movements and trajectories can be defined such as but not limited to tilting movements, movements away or towards the user, movements to the right or left of the user, movements up and down relative to the user, circular movements clockwise or anti clockwise, spinning movements clockwise or anti clockwise, shaking movements, no movement or a combination of such movements. The predetermined movement will lead to acceleration of the device, the acceleration can be positive or negative and can be in all directions of a 3-axis x, y, z coordinate system relative to the user or relative to the hand held device. The acceleration will be detected by at least one accelerator in the device. The detected acceleration is wireless transmitted to a display device. The predetermined movement can be determined by the manufacturer of the device and/or by the user.

The term "display device" means a device that is wireless paired or connected to the hand help device. The display device is used to control the hand held device and to display results measured by the hand held device. The display device generally contains a screen or projects a screen onto a reflective surface for viewing. The display device can be a smartphone, a tablet computer or a personal computer or a notebook computer or a projector or a dedicated device build to work with the hand held device. The display device runs software to control the hand held device and to analyze and display results obtained with the hand held device. The software can be an applet or any type of software.

The term "screen navigation" or "screen control" means operations such as but not limited to scrolling of a screen, opening a new screen, selecting a function or tap on a screen, taping a tap, go through a sequence of taps or functions for selection, switch to cursor movement and back, editing a screen or combinations thereof. In general the screen navigation can be used to start a program, navigate and call functions of a computer program and closing a program. The screen navigation is performed on the screen of the display device.

The term "software" in the context of this invention means the software that receives the information of the at least one accelerometer in the hand held device and computes a trajectory of the movement of the device by the user and compares the computed trajectory with predetermined movements or trajectories and executes the respective screen navigation function on the display device. Typically the software runs on the display device. The software may also run partially in the hand held device for example to analyze the movement.

The term "measurement" means the process of using the "hand held laboratory device" to analyze a sample and thereby determining the concentration of an analyte or obtaining a result with the device.

The term "analyte" means the species to be analyzed by performing a measurement in or on a sample. Typically to measure a chemical compound such as but not limited to proteins, peptides, nucleic acids, DNA, RNA, lipids, pH value, explosives, gases, drugs, metabolites such as but not limited to glucose, billirubine, dextran or a biological compound such as but not limited to microorganism, virus, cells, algae or a biomarker or a pH value or tubidimetry or nephleometry or a color or a mixtures thereof. In the context of the current invention the term "analyte" also refers to a physical parameter such as light intensity, x-ray intensity, electrical potential or current or conductivity or radiation or radioactivity or temperature or pressure or refractive index.

DETAILED DESCRIPTION OF THE INVENTION

The current invention discloses a system consisting of a hand held laboratory device and a display device and a set of predetermined movements to control screen navigation on the display device such as a smart phone or tablet computer or projector. First a hand held laboratory device such as a hand help photometer is provided. The hand held device contains at least one accelerometer and a wireless transmitter. Second a display device such as a smart phone is provided. The display device runs a software to receive data of the at least one accelerometer. From the accelerometer data the acceleration and the trajectory of the hand held device caused by user movements of the hand held device is calculated. Then the software compares the calculated trajectories with a predetermined set of movements or trajectories in its memory. The user initiated movement or trajectory is identified and the respective screen navigation operation is executed on the screen of the display device.

In a general embodiment the handheld laboratory device is wireless and comprises measurement means and at least one accelerometer and wherein a movement of the handheld laboratory device in a 3 dimensional x,y,z coordinate system is detected by the at least one accelerometer and is wireless relayed to a display device to compute instructions for the handheld laboratory device to operate the measurement means. Optional the data from the at least one accelerometer is pre-analyzed in the handheld laboratory device to reduce the amount of transmitted data and/or to determine the predetermined movement.

A system for screen navigation composed of:
a) A hand held laboratory device containing at least one accelerometer
b) a display device containing a screen,
c) and a software running on the display device accessing a set of predetermined movements and able to receive acceleration data from the hand held laboratory device and able to compute a movement of the hand held laboratory device from the acceleration data and able to compare such computed movements with the predetermined set of movements and matching similar movements and able to initiate a screen navigation function on the display device linked to the matched movement.

The current invention also discloses a method to use a hand held laboratory device to control screen navigation on a display instrument such as a smart phone or tablet computer by using predetermined movements of the hand held device to initiate and control screen navigation. Several predetermined movements and trajectories can he defined such as tilting movements, movements away or towards the user, movements to the right or left of the user, movements up and down relative to the user, circular movements clockwise or anti clockwise, spinning movements clockwise or anti clockwise, shaking movements, no movement (stand still) or a combination of such movements. The predetermined movements can be stored in a memory. Typically a set of predetermined movements is defined. Each predetermined movement is correlated to a screen navigation function. For example a right movement initiated the display of the next screen and a left movement the display of the previous screen. Predetermined movements can also switch on or off the screen navigation function. A predetermined movement of the hand held device by the user will lead to acceleration of the device, the acceleration can be positive or negative and can be in all directions of a 3-axis x,y,z coordinate system relative to the user or relative to the hand held device or relative to a fixed coordinate system in space. The acceleration is detected by at least one accelerator in the device and wireless transmitted to a display device. The software running on the display device is comparing the user movement with the set of predetermined movements stored in the display device memory. Alternatively the movements can be compared in the hand held device and the matching movement is transmitted. The software then selects the matching predetermined movement. The match might be 100% or less than 100%. A threshold percentage of matching can be defined at which a match is confirmed. After selecting or matching the correct predetermined movement a respective screen navigation operation such as scrolling of a screen or selecting a function on the screen is initiated. This function, for example, could control the hand held device and for example initiate a measurement which is performed by the hand held device.

A method for the control of a hand held laboratory device involving the steps of:
a) Providing a hand held laboratory device containing at least one accelerometer
b) Providing a display device containing a screen,
c) Providing a software running on the display device,
d) Providing a set of predetermined movements stored in a computer memory on the display device,
e) and wherein the display device is receiving acceleration data from the hand held laboratory device and computes the movement of the hand held laboratory device from the acceleration data and compares such computed movements with the predetermined set of movements and is matching similar movements and initiates a screen navigation function on the display device linked to the matched movement.
f) And wherein this function may control the hand held laboratory device to perform a measurement or other operations of the hand held laboratory device.

A general aspect of the current invention is to use screen navigation functions to control the hand held laboratory device by a display device comprising a screen. This method comprising the steps of receiving acceleration data from at least one accelerometer of the hand held laboratory device, computing a movement of the hand held laboratory device from the acceleration data and comparing the computed movement with a predetermined set of movements and where the computed movement matches or is similar to one of the predetermined set of movements, initiating a screen navigation function on the screen of the display device corresponding to the matched predetermined movement and/or initiating a control function in the hand held laboratory device corresponding to the matched predetermined movement. To illustrate this aspect an example for wavelength control in a hand held photometer device is given in the following. In this example the user may scroll to a number of tabs wherein each tab is representing a different wavelength, such as the wavelength 260, 280 and 600 nm. The user may use movements of his hand and the device to control screen navigation and to select a tab, for example the 280 nm tab on the display device. After selection the display device sends a control function to the hand held device to switch on the 280 nm light source in the hand held device to perform a measurement at the selected wavelength. A similar method can be used to control any other function of the hand held laboratory device. Control functions initiated in the hand held laboratory device are all functions necessary to use the device to carry out a measurement. Examples of such initiated control functions in the hand held device are: Switch the device on or off, start a measurement, stop a measurement, send data to the display device, switch on or of a light source, switch on or of a sensor, switch on or of an indicator light, determine the status of a button, receive data from the display device, display information on a display in the hand held device, send battery status information, send error messages, and mixtures thereof. Most advantageously, the method and system of the current invention allows the control of a screen on a display device and consequently the selected screen function controls a hand held laboratory device.

In another embodiment of the present invention the software includes a learning function. The user may execute a movement and stores the movement in a computer memory as a predetermined movement and links the movement to a screen navigation function. This function allows the user to create a user defined set of predetermined movements or to let the software "learn" the trajectory of one particular user for existing predetermined movements.

In another embodiment of the current invention the measurement results obtained may be displayed on more than one display device such as a repeater. This feature is useful for educational or teaching purposes. The same or modified software may run on the repeater units. The repeater unit could be a smart phone, a tablet computer or a PC or a projector. In general there is no limit on the number of repeater units. The repeater unit could be in bluetooth paring distance to the hand held device or to the display device or a remote repeater connected to the internet or wireless.

In another embodiment of the current invention the predetermined movement may be used to logon onto a device or software. The user may define a 3-dimensional movement in space as his personal "password" to logon onto the device.

In another embodiment of the current invention related to a photometer hand held device with a disposable measurement tip a predetermined movement indicates the pick up or the disposal of the photometric measurement tip and indicate the status on the screen of the display device. Any movement of the user other than a predetermined movement may be analyzed by the software to detect actions performed by the user such as picking up a tip or disposing a tip or picking up the hand held device or placing the hand held device into its holder.

For all embodiments of the current invention, optionally the user may press a button on the hand held device to indicate the time at which a predetermined movement takes place. Instead pressing a button other indications such as a certain sequence of presses or pressing a tap on the display device may be used alternatively.

For all embodiments of the current invention, optionally and in addition a radio frequency tag or other means such as light or the signal strength of a Bluetooth device can be used to determine the relative position and distance between the hand held device and accessories placed on the lab bench. The position determined by a radio frequency tag or other means can be used to zero in a 3 dimensional coordinate system. Accessories are boxes holding measurement tips; boxes for disposal or the holder and/or charger for the hand held device or the display unit. In general a 3 dimensional coordinate system can be relative to the user or relative to the hand held device or relative to the lab bench or relative to an accessory. Alternatively an absolute coordinate system such as provided by global positioning system (GPS) can be used. If a coordinate system relative to the display unit is used and the display unit contains a GPS receiver the relative coordinate system can be transformed into an absolute coordinate system. This is in particular important for outdoor measurements to localize the exact sample coordinates which can be saved together with the sample measurement. If the relative or absolute coordinate system is fixed once the relative or absolute position of the hand held device during operations can be determined by analyzing the acceleration of 3 accelerometers for x, y and z dimensions in space. An absolute fix of the position can be performed at the time the hand held device is placed in its holder or charger station and the absolute position of the holder or charger station is known.

Most advantageously, the current invention solves several limitations of current hand held laboratory devices such as 1) Hand free operation of a control or display device while using gloves or working in a fume hood or lateral flow bench under sterile conditions. This is of uttermost importance in a laboratory environment. The invention increases the safety of laboratory work. Current devices would require the user to use its contaminated gloves to operate a device or the user must remove its gloves and take on a new glove; both practices are unsafe. The invention also reduces the risk of contamination while working in a sterile environment such as a laminar flow bench. The display device does not need to be under the flow bench, it could be attached to the transparent screen of the flow bench with a holder in easy viewing distance to the user. The user can keep his hand under the flow bench at all times reducing contamination risk. 2) The invention is boosting productivity and ease of use by performing screen operation with a quick move of the hand. 3) The invention creates continues workflows using a hand held device, non-interrupted by touching a screen. 3) The invention also adds a "fun element" into the operation of a hand held device making it more desirable for the user to use.

EXAMPLES

Examples are provided for the better understanding of the current invention and should not be interpreted to limit the current invention.

Example 1

This example discloses a possible set of predetermined movements and trajectories to initiate screen navigation. The set of movements only serves as an example and is not understood to limit the current invention. Other movements can be defined and used to initiate different screen navigation functions. Also a user may define its own set of functions freely. The following predetermined movements can be used for screen navigation:

A movement away from the user to tap a button. This movement is similar to tap a physical button.

A movement towards the user to scroll through a sequence of taps.

A movement to the right to go to the previous screen. This movement is similar to turn over a page in a book and go to the previous page.

A movement to the left to go to the next screen. This movement is similar to turn over a page in a book and go to the next page.

A cycling movement clockwise to scroll a screen down

A cycling movement anti clockwise to scroll a screen up

Two short movements to the user to switch between screen movements and mouse movements.

The screen navigation function can be also switched on or off. This is important to not cause uncontrolled screen operations when the device is transported or the user walks around with the device. The on and off switching can be performed on the display unit by a tab of the user or by using additional predetermined movements.

DETAILED DESCRIPTION OF THE DRAWINGS

Drawings are provided for the better understanding of the current invention and should not be interpreted to limit the current invention.

FIGS. 2A and 2B: Depicts a method of the current invention to control the screen of a display device (i) by movements of a hand held laboratory device (ii). In this example the coordinate system is the user or a fixed 3 dimensional coordinate system. It is assumed that the user is not moving during operation of the device. It should be noted that the current invention also works in a coordinate system relative to the user when the user is at a constant movement, e.g. the user is on a ship, or an airplane or land vehicle with a constant velocity because as long the velocity does not change no acceleration will be detected. In an advanced embodiment of the current invention a "velocity noise filter" or compensation can be used to discard random fluctuations of velocity observed in any moving vehicle. In such an advanced embodiment the GPS information from the display device, which is not undergoing the movement of the hand held laboratory device caused by the movement of the users hand holding the device but undergoing the movement of the user relative to a fixed coordinate system in space can be used to offset or eliminate random velocity movements or accelerations caused by using the device in a vehicle, ship, airplane, train, spaceship or submarine. To obtain the relative acceleration or movement of the device relative to the user the GPS acceleration or movement from the display device is deducted from the acceleration or movement of the hand held device. In the following an example of a typical operation of screen navigation of the current invention is provided. The view is the view relative to the user. FIG. 2A depicts: (a) The user performs a movement to the left to go to the next screen. (b) The user performs a cycling movement clockwise to scroll a screen down. (c) The user performs a movement towards himself to select the next function tab. Continuation on FIG. 2B: (d) The user may perform several movement towards himself to select the desired function tab. (e) The user performs a movement away from himself to tap on the selected function and start a function "n". Consequently the display device may send the control function "n" command to the hand held laboratory device and initiate control function "n" in hand held laboratory device. Such initiated control functions in the hand held device are typically physical processes or logical processes such as switch the device on or off, start a measurement, stop a measurement, send data to the display device, switch on or of a light source, switch on or of a sensor, switch on or of an indicator light, determine the status of a button, receive data from the display device, display information on a display in the hand held device, send battery status information, send error messages, and mixtures thereof.

Figure 1:
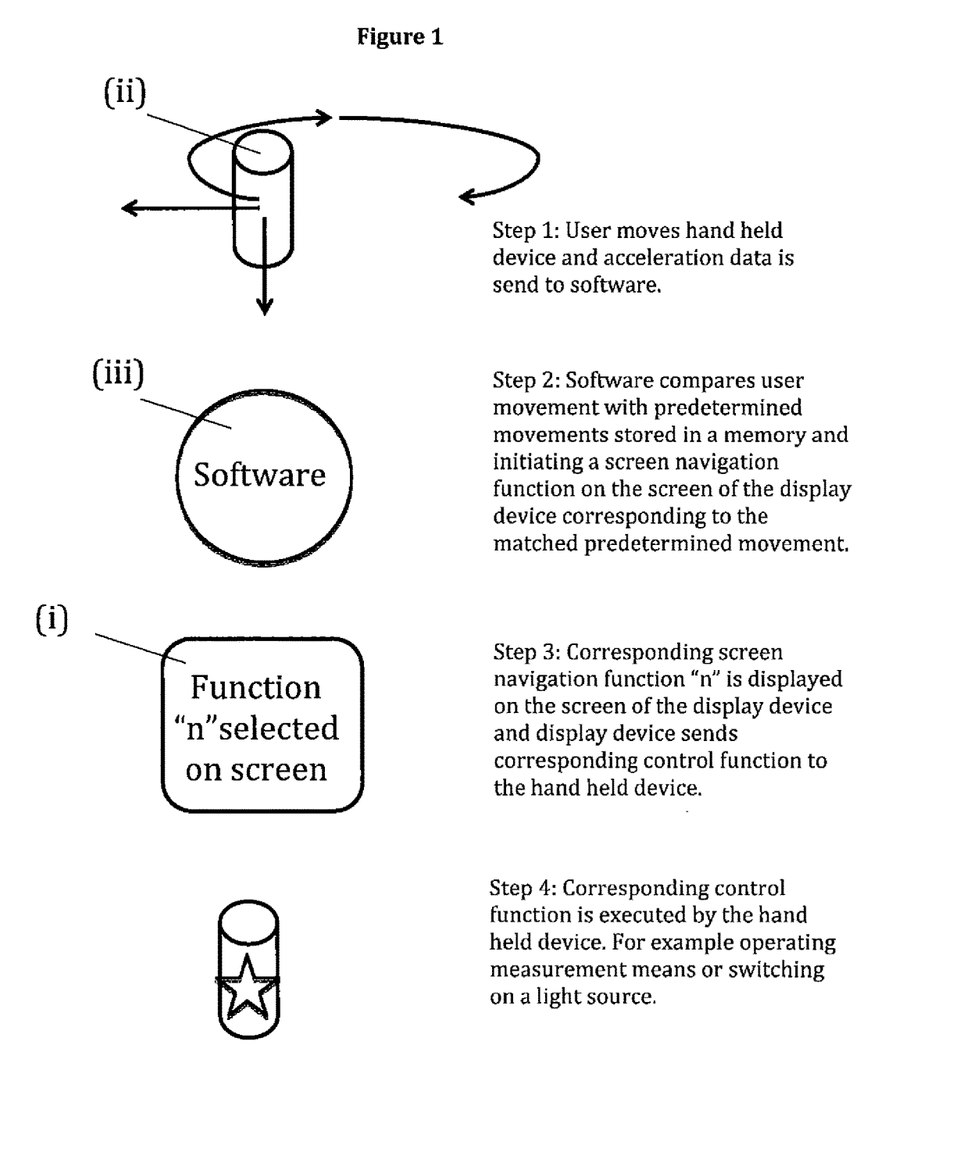
FIG. 1: Depicts a system and method steps 1 to 4 of the current invention to control the screen of a display device (i) by movements of a hand held laboratory device (ii) by matching a user hand movement or the movement of the hand held device with a predetermined movement stored in a memory by a software (iii) and consecutively initiation a control function in the hand held device.
Figure 2A:
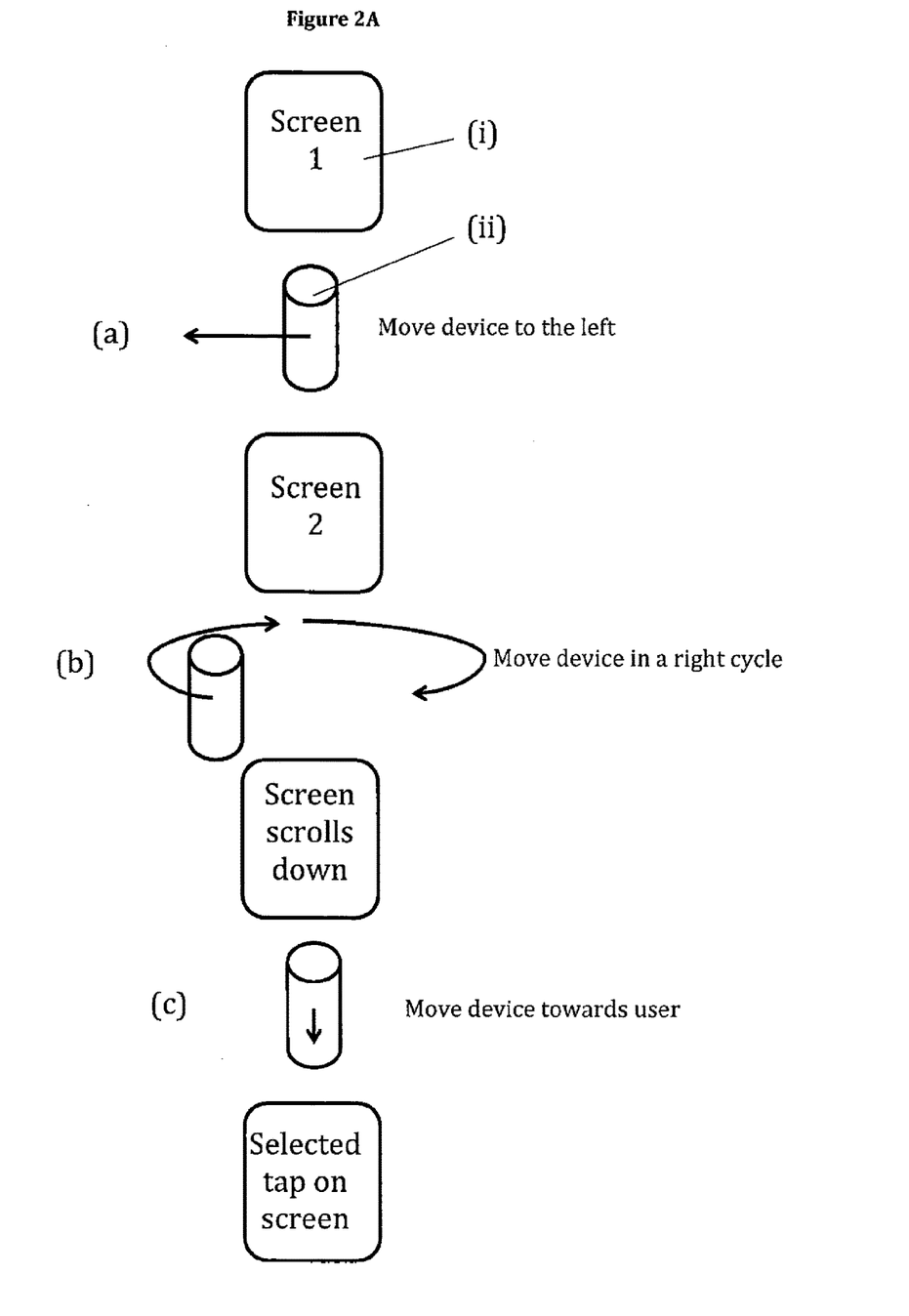
Figure 2B:
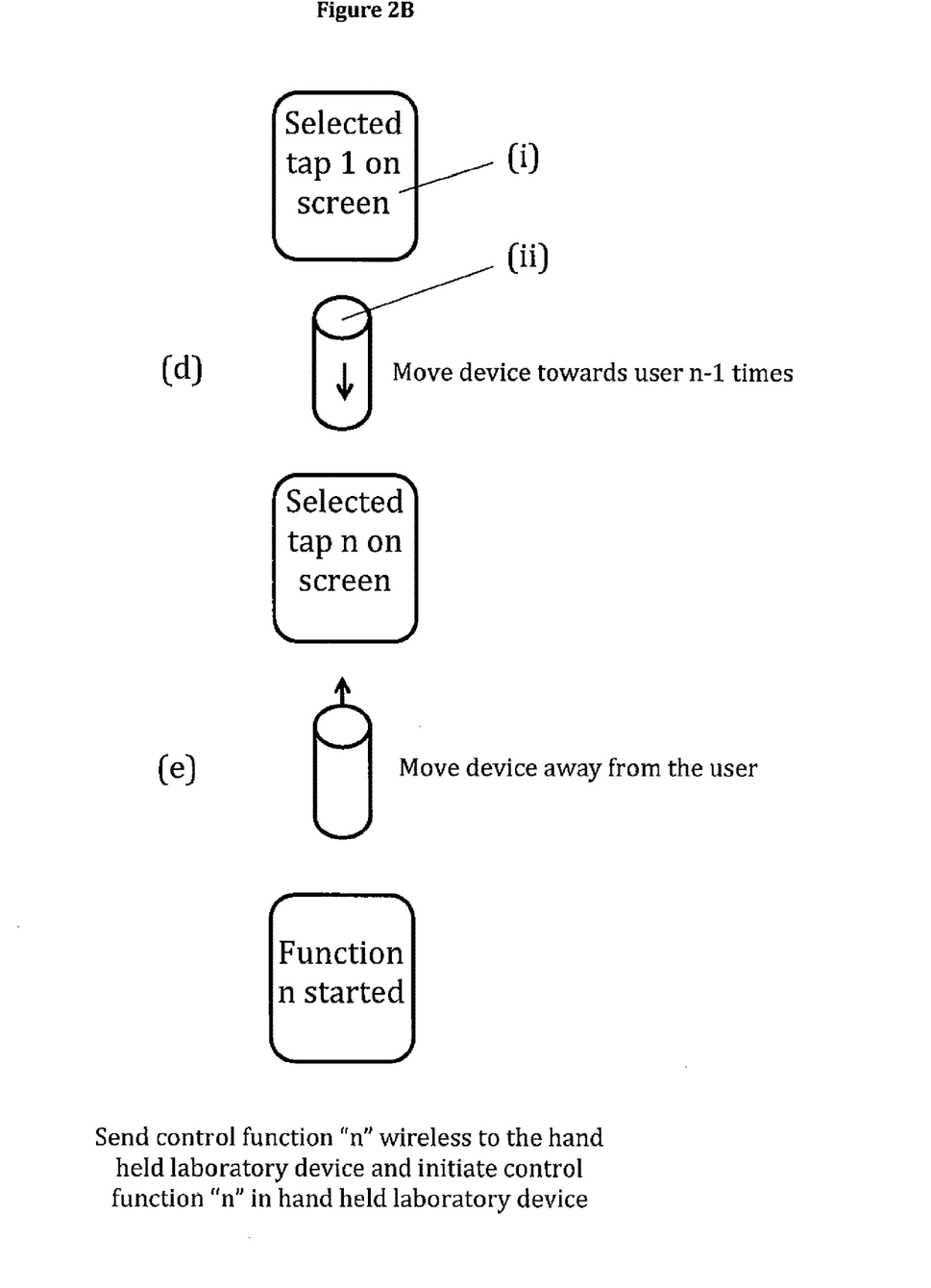

In contrast to the current control of hand held devices wherein all controls are within the hand held device and directly input by an operator or an external wired or wireless device directly controls the hand held device by input from an operator; in the current invention the operator of the hand held device first controls an external device such as a display device by predetermined movements of the hand held device in a 3 dimensional space and then the external or display device controls the hand held device for example to initiate a measurement. The external device functions as a "relay station" to receive compute and sends data to the handheld device. Advantageously, in the current invention the operator do not need to make a direct or physical input into the display device while holding the hand held device.

Aspects of the invention may be understood with reference to the following paragraphs:

1. A method for screen navigation involving the steps of:
   a) Providing a hand held laboratory device containing at least one accelerometer
   b) providing a display device containing a screen,
   c) providing a software running on the display device,
   d) providing a set of predetermined movements stored in a computer memory on the display device,
   e) and wherein the software running on the display device is receiving acceleration data from the hand held laboratory device and computes the movement of the hand held laboratory device from the acceleration data and compares such computed movements with the predetermined set of movements and is matching similar movements and initiates a screen navigation function on the display device linked to the matched movement.

The method of paragraph 1, wherein the hand held laboratory device is a photometers, a pH meters, a volt, conductivity or ampere meter; a luminometer, a gas detection meter, a pipette, a turbidity meter, a nephleometer, a temperature or pressure meter, a x-ray detection meter, a scanners for drugs or explosives, a glucose meter, a biosensor, a point of care diagnostic device, a blood pressure meter or mixtures thereof.

The method of paragraph 1, wherein the display device is a smartphone, a tablet computer or a personal computer or a notebook computer or a dedicated device built to work with the hand held device.

The method of paragraph 1, wherein the software receives the information of the at least one accelerometer in the hand held device and computes a trajectory of the movement of the device caused by the users hand movements and compares the computed trajectory with predetermined movements or trajectories to match the computed trajectory with one predetermined movement and executes the respective screen navigation function on the display device.

The method of paragraph 1, wherein the movement or acceleration of the display devices GPS data is deducted from the movement or acceleration of the laboratory hand held devices accelerator data.

The method of paragraph 1, wherein the predetermined movement is a tilting movements, movements away or towards the user, movements to the right or left of the user, movements up and down, circular movements clockwise or anti clockwise, spinning movements clockwise or anti clockwise, shaking movements, no movement (still stand) or a combination of such movements.

The method of paragraph 1, wherein the predetermined movement are computed relative to the hand held laboratory device or relative to the user or relative to a fixed coordinate system in space.

The method of paragraph 1, wherein the screen navigation function is the scrolling of a screen, opening a new screen, selecting a function or tap on a screen, taping a tap, browse through a sequence of taps or functions for selection, switch to cursor movement and back, editing a screen, start a program, closing a program.

2. A system for screen navigation composed of:
   a) A hand held laboratory device containing at least one accelerometer
   b) a display device containing a screen,
   c) and a software running on the display device accessing a set of predetermined movements and able to receive acceleration data from the hand held laboratory device and able to compute a movement of the hand held laboratory device from the acceleration data and able to compare such computed movements with the predetermined set of movements and matching similar movements and able to initiate a screen navigation function on the display device linked to the matched movement.

3. A system for controlling a hand held laboratory device composed of:
   a) A hand held laboratory device containing at least one accelerometer and measurement means,
   b) a display device containing a screen,
   c) and a software running on the display device accessing a set of predetermined movements and able to receive acceleration data from the hand held laboratory device and able to compute a movement of the hand held laboratory device from the acceleration data and able to compare such computed movements with the predetermined set of movements and matching similar movements and able to initiate a screen navigation function on the display device linked to the matched movement. And wherein the function controls the measurement means within the hand held laboratory device.

The invention claimed is:
1. A system for controlling a handheld laboratory device comprising:

a) a handheld laboratory device containing at least one accelerometer measurement means, and a wireless transmitter; and
b) a display device comprising a screen, the display device being remote from the handheld laboratory device, wherein the measurement means are operable by
recording acceleration data from an accelerometer of the handheld laboratory device corresponding to a movement of the handheld laboratory device by a user;
computing a movement of the handheld laboratory device from the acceleration data;
transmitting the computed movement from the handheld laboratory device to a display device remote from the handheld laboratory device;
comparing the computed movement with a predetermined set of movements, where the computed movement matches or is similar to one of the predetermined set of movements;
initiating a screen navigation function corresponding to the matched predetermined movement;
transmitting a control function corresponding to the screen navigation function from the display device to the handheld laboratory device; and
initiating a control function in the handheld laboratory device via the screen navigation function.

2. A display device comprising a screen,
the display device being
remote from a handheld laboratory device and operable to perform a measurement on the handheld laboratory device by
comparing a computed movement with a predetermined set of movements, where the movement matches or is similar to one of the predetermined set of movements;
initiating a screen navigation function corresponding to the matched predetermined movement on a display device remote from the handheld laboratory device;
initiating a control function in the handheld laboratory device via the screen navigation function, wherein the computed movement is computed by the handheld laboratory device;
recording acceleration data from an accelerometer of the handheld laboratory device; and
computing a movement of the handheld laboratory device from the acceleration data.

3. A display device according to claim 2, comprising at least one position sensor and an accelerator, wherein the display device is operable to use the movement or acceleration of the display device for computing the movement of the handheld laboratory device.

4. A handheld laboratory device comprising measurement means and at least one accelerometer, and a wireless transmitter, wherein
the measurement means are operable by recording acceleration data from the accelerometer corresponding to a movement of the handheld laboratory device by a user;
computing a movement of the handheld laboratory device from the acceleration data;
transmitting the computed movement from the handheld laboratory device to a display device remote from the handheld laboratory device; and receiving from the display device initiation of a control function,
wherein the display device is operable by comparing the computed movement with a predetermined set of movements, where the computed movement matches or is similar to one of the predetermined set of movements; initiating a screen navigation function corresponding to the matched predetermined movement; and transmitting a control function corresponding to the screen navigation function from the display device to the handheld laboratory device.

5. A handheld laboratory device according to claim 4, wherein the measurement means comprise one or more of a photometer, a spectrometer, a pH meters, a volt, conductivity or ampere meter; a luminometer, a gas detection meter, a pipette, a turbidity meter, a nephleometer, a temperature or pressure meter, a x-ray detection meter, a scanners for drugs or explosives, a glucose meter, a biosensor, a point of care diagnostic device, a blood pressure meter, or mixtures thereof.

6. A method of operating a handheld laboratory device, the method comprising the steps of
recording acceleration data from an accelerometer of the handheld laboratory device corresponding to a movement of the handheld laboratory device by a user;
computing a movement of the handheld laboratory device from the acceleration data;
transmitting the computed movement from the handheld laboratory device to a display device remote from the handheld laboratory device;
comparing the computed movement with a predetermined set of movements, where the computed movement matches or is similar to one of the predetermined set of movements;
initiating a screen navigation function corresponding to the matched predetermined movement;
transmitting a control function corresponding to the screen navigation function from the display device to the handheld laboratory device; and
initiating a control function in the handheld laboratory device via the screen navigation function.

7. A method according to claim 6, comprising computing the movement of the handheld laboratory device by computing a trajectory of the movement of the handheld laboratory device.

8. A method according to claim 7, comprising comparing the computed trajectory with predetermined movements or trajectories to match the computed trajectory with one predetermined movement.

9. A method according to claim 6, comprising receiving acceleration or movement data from at least one of a position sensor and an accelerator of the display device, and using the movement or acceleration of the display device in computing the movement of the handheld laboratory device.

10. A method according to claim 6, wherein the predetermined movements are one or more of a tilting movement, movements away or towards the user, movements to the right or left of the user, movements up and down, circular movements clockwise or anti clockwise, spinning movements clockwise or anti clockwise, shaking movements, no movement (still stand), or a combination thereof.

11. A method according to claim 6, comprising computing the movement of the handheld laboratory device relative to the handheld laboratory device or relative to the user or relative to a fixed coordinate system in space.

12. A method according to claim 6, wherein the screen navigation functions are one or more of scrolling of a screen, opening a new screen, selecting a function or a tap on a screen, tapping a tap, browsing through a sequence of taps or functions for selection, switching to cursor movement and back, editing a screen, starting a program, closing a program, and login on or off of a user.

13. A method according to claim 6, wherein the control function in the handheld laboratory device is to switch the device on or off, start a measurement, stop a measurement, send data to the display device, switch on or of a light source, switch on or of a sensor, switch on or of an indicator light, determine the status of a button, receive data from the display device, display information on a display in the handheld device, send battery status information, send error messages, and mixtures thereof.

14. A method according to claim 6, comprising transmitting data from the accelerometer of the handheld laboratory device to the display device.

15. A program operable when run on the handheld laboratory device and/or the display device to perform a method according to claim 6.

* * * * *